United States Patent [19]

Borch et al.

[11] Patent Number: 5,472,956
[45] Date of Patent: Dec. 5, 1995

[54] PHOSPHORAMIDATES USEFUL AS ANTITUMOR AGENTS

[75] Inventors: Richard F. Borch, Pittsford; James P. Schmidt, Rochester, both of N.Y.

[73] Assignee: Research Corporation Technologies, Inc., Tucson, Ariz.

[21] Appl. No.: 184,305

[22] Filed: Jan. 21, 1994

Related U.S. Application Data

[62] Division of Ser. No. 55,964, Apr. 30, 1993, Pat. No. 5,306,727.

[51] Int. Cl.$^6$ .................................................. C07F 9/02
[52] U.S. Cl. .................................. 514/95; 514/90; 514/91; 514/94; 514/99; 514/231.5; 514/232.2; 514/235.8; 514/398; 514/426; 514/472; 514/447; 544/84; 544/139; 544/146; 544/152; 548/119; 548/413; 549/6; 549/218
[58] Field of Search ...................... 549/6, 218; 548/119, 548/413; 514/447, 472, 398, 426, 231.5, 232.2, 235.8, 90, 94, 91, 95, 99; 544/84, 139, 146, 152

[56] References Cited

U.S. PATENT DOCUMENTS

| | | | |
|---|---|---|---|
| 4,908,356 | 3/1990 | Borch et al. | 514/90 |
| 4,997,822 | 5/1991 | Hohorst et al. | 514/90 |
| 5,190,929 | 3/1993 | Borch et al. | 514/80 |

FOREIGN PATENT DOCUMENTS

| | | | |
|---|---|---|---|
| 0235661 | 9/1987 | European Pat. Off. . | |
| 891148 | 11/1989 | WIPO | 548/443 |

OTHER PUBLICATIONS

CA 69(19):76898u Benzyl phosphorodiamidates. Kawakami et al., p. 7180, 1968.
CA 112(21):198797n Phosphoramides useful as antitumor agents. Borch et al., p. 754, 1990.
CA 115(17):183451h Synthesis . . . analogs. Borch et al., p. 945, 1991.
CA 115(19):208082d Nitro . . . cells. Firestone et al., p. 1033, 1991.
84th Annual Meeting of the American Association for Cancer Research, Orlando, Fla., USA, May 19–22, 1993, Proc. Am. Assoc. Cancer Res. Annu. Meet. 34, Mar. 1993, p. 267, Abstract 1987, R. F. Borch et al., "Synthesis and Cytotoxicity of Novel Hypoxia–Selective Phosphoramidates".

*Primary Examiner*—Joseph K. McKane
*Attorney, Agent, or Firm*—Schwegman, Lundberg & Woessner

[57] ABSTRACT

Cyclophosphamide analogs are provided of the general formula:

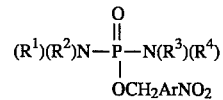

wherein $R^1$ and $R^2$ are each $(C_2–C_6)$alkyl, substituted with a leaving group such as halo or alkylsulfonyl, $R^3$ and $R^4$ are the same as $R^1$ and $R^2$ or are H and Ar is a heteroaromatic ring and the pharmaceutically acceptable salts thereof.

12 Claims, No Drawings

PHOSPHORAMIDATES USEFUL AS ANTITUMOR AGENTS

The present invention was made with the support of the National Institutes of Health under Grant No. ROI CA 34619. The Government has certain rights in the invention. This is a division of application Ser. No. 08/055,964, filed Apr. 30, 1993 now U.S. Pat. No. 5,306,727.

BACKGROUND OF THE INVENTION

Cyclophosphamide (also known as cytoxan) (I) is one of the most widely used anti-cancer drugs.

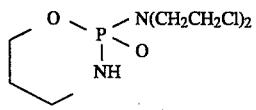
(I)

It is generally administered in combination with a number of other drugs to treat a wide variety of hematologic and solid tumors. However, there are several features of the drug that limit its clinical utility. First, the drug requires activation in the liver to produce metabolites that are toxic to cancer cells. Second, the drug is specifically toxic to the urinary bladder and also displays the bone marrow toxicity typical of the alkylating agent class of anti-cancer drugs. Third, cyclophosphamide is a potent suppressor of the immune system at the doses used to treat cancer, thus decreasing the infection-fighting ability of patients already debilitated by their disease. Finally, repeated use of cyclophosphamide frequently results in the development of resistance to the drug by a patient's cancer cells, thus rendering the drug ineffective.

In an attempt to circumvent at least some of these disadvantages, a number of analogs have been disclosed, which preserve at least some of the structural features of cyclophosphamide. For example, published PCT application WO 89/11484, by Research Corporation Technologies, Inc. discloses phosphoramides of the general formula:

$$\begin{array}{c} O \\ \| \\ R_1R_2N-P-N(CH_2CH_2Cl)_2 \\ | \\ O-CHR \\ | \\ CHR_3R_4 \end{array}$$

wherein $R_1$ and $R_2$ may be H or haloalkyl, R may be a nitro-substituted heteroaromatic group and $R_3$ and $R_4$ may independently be hydrogen, $(C_1-C_{10})$alkyl or an electron-withdrawing group, such as $CO_2Et$. Although these compounds are disclosed to be desirably cytotoxic in hypoxic cells, the most active compounds disclosed comprise at least one electron-withdrawing group at $R_3$ or $R_4$, which necessarily complicates their synthesis and reduces their stability. See also, Borch et al. (U.S. Pat. Nos. 4,908,356 and 5,190,929).

Therefore, a continuing need exists for cyclophosphamide analogs which are highly cytotoxic against a wide variety of tumor cells, while being stable and easy to prepare.

SUMMARY OF THE INVENTION

The present invention provides antineoplastic phosphoramide compounds of the general formula (II):

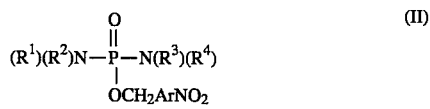
(II)

wherein $R^1$ and $R^2$ are individually $(C_2-C_6)$alkyl substituted with halogen, $(C_1-C_4)$alkoxy, $(C_6-C_{12})$aryloxy, cyano, $(C_1-C_4)$alkoxycarbonyl, $(C_1-C_4)$alkylsulfonyl, $(C_6-C_{12})$arylsulfonyl, $(C_1-C_4)$perfluoroalkylsulfonyl, $(C_1-C_4)$alkylsulfinyl, $(C_6-C_{12})$arylsulfinyl, or $R^1$ and $R^2$ taken together with N are a morpholino ring; $R^3$ and $R^4$ are the same as $R^1$ and $R^2$ or are individually H; and Ar is a nitrogen-, sulfur- or oxygen-containing heteroaromatic ring; preferably, Ar is a 5- or 6-membered heteroaromatic ring comprising 1–3N, S or non-peroxide O atoms in the ring, wherein each ring N atom is unsubstituted or is substituted with $(C_1-C_4)$alkyl.

Representative compounds of the present invention are depicted on Table I, below.

TABLE 1

Representative Compounds

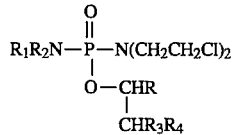

| Compound | $ArNO_2$ | $R^1 = R^2$ | $R^3 = R^4$ |
|---|---|---|---|
| 1 | thiophene-NO₂ | $ClCH_2CH_2-$ | $ClCH_2CH_2-$ |
| 2 | furan-NO₂ | $ClCH_2CH_2-$ | $ClCH_2CH_2-$ |
| 3 | N-methylimidazole-NO₂ | $ClCH_2CH_2-$ | $ClCH_2CH_2-$ |
| 4 | N-methylpyrrole-NO₂ | $ClCH_2CH_2-$ | $ClCH_2CH_2-$ |
| 5 | thiophene-NO₂ | $BrCH_2CH_2-$ | $BrCH_2CH_2-$ |
| 6 | thiophene-NO₂ | $BrCH_2CH_2-$ | H |
| 7 | thiophene-NO₂ | $ClCH_2CH_2-$ | H |
| 8 | furan-NO₂ | $ClCH_2CH_2-$ | H |

TABLE 1-continued

Representative Compounds $$\begin{array}{c} O \\ \| \\ (R^1)(R^2)N\text{—}P\text{—}N(R^3)(R^4) \\ | \\ OCH_2ArNO_2 \end{array}$$

| Compound | ArNO$_2$ | R$^1$ = R$^2$ | R$^3$ = R$^4$ |
|---|---|---|---|
| 9 | (furan with NO$_2$) | BrCH$_2$CH$_2$— | H |

The present phosphoramidate compounds circumvent one or more of the problems with cyclophosphamide discussed hereinabove. First, the present compounds are more cytotoxic under oxygen-deficient conditions than under normal aerobic conditions. Therefore, unlike cyclophosphamide which is cytotoxically activated in the liver, the present compounds can become selectively cytotoxic in hypoxic cells. Hence, oxygen-deficient tumor cells can be selectively destroyed by concentrations of these compounds which do not affect non-cancerous cells as severely. Second, these compounds are relatively non-toxic to the urinary bladder. Third, the compounds of the present invention are effective in treating mammalian tumors that have developed resistance to cyclophosphamide.

Hypoxic cells in tumors are generally resistant to radiation and chemotherapy and thus represent a population of cells that are very difficult to eradicate. Most mammalian cells operate under conditions of oxygen excess and utilize oxidative metabolism. Hypoxic cells, however, represent a reducing environment. Thus, a prodrug designed to be activated by the reducing environment inside such cells can deliver a cytotoxic species specifically to the tumor cell and thus can offer a potential therapeutic advantage over known compounds. The compounds of the present invention are prodrugs that can liberate the cytotoxic phosphoramidate anion or analog (a cytotoxic metabolite derived from cyclophosphoramidate) when exposed to the reducing environment of the hypoxic cell. The compounds of the present invention are selectively less cytotoxic under normal aerobic conditions but highly cytotoxic under hypoxic conditions.

The effectiveness of these compounds is believed to result from the reduction of the nitro groups in the hypoxic cells. It is believed that this reduction facilitates expulsion of a cytotoxic phosphoramide mustard moiety. Once released, the phosphoramide mustard acts as a DNA alkylating agent. Thus, the present compounds can be classified as "bioreductive alkylating agents."

The present invention also provides a therapeutic method comprising administering to a mammal afflicted with a tumor an amount of a compound of formula (II) effective to inhibit the growth of the cells of said tumor. Preferably, the afflicted mammal is a human cancer patient and the compound of formula II is administered as a pharmaceutical unit dosage form. The compounds of formula (II) can also be used to identify and characterize neoplastic hypoxic and aerobic cell lines.

DETAILED DESCRIPTION OF THE INVENTION

As used herein, the term "alkyl" includes straight- or branched-chain alkyl. Preferably, the alkyl groups are (C$_2$–C$_3$) alkyl, most preferably ethyl. As used herein, the term "aryl" includes mono- or bis- alkyl-substituted aryl, such as tolyl and xylyl; and Ar(C$_1$–C$_4$)alkyl, such as benzyl or phenethyl. Preferably, aryl is phenyl, tolyl or naphthyl.

Heteroaromatic rings are aromatic rings containing up to 4 ring heteroatoms and up to 18 ring atoms. Representative heteroaromatic rings include thiophene, benzothiophene, naphthothiophene, trianthrene, furan, benzofuran, isobenzofuran, pyran, chromene, xanthene, phenoxathiin, pyrrole, imidazole, pyrazole, pyridine, pyrazine, triazole, tetrazole, pyrazine, triazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, phenanthroline, phenazine, isothiazole, phenothiazine, oxazole, isoxazole, furazan, phenoxazine and the like. The nitro (NO$_2$) group may be substituted on any position of the ring but is preferably not on a ring heteroatom. Preferred heteroaromatic rings have a 5- or 6-membered heteroaromatic ring which may or may not be fused to an aromatic ring such as a benzo ring. Preferred ArNO$_2$ groups include nitrothiophenes, e.g., 2-nitrothiophene or 3-nitrothiophene, nitropyridines, nitroquinolines, nitroisoquinolines, nitropyrroles, nitrofurans and nitroimidazoles. Preferably, at least one of the ring nitrogen atoms is substituted with a (C$_1$–C$_4$)alkyl group, most preferably with methyl, as in the case of the preferred 1-methyl-5-nitro-2-imidazoyl or 1-methyl-4-nitro-2-pyrrolo groups. Halogen, or halo, groups include F, Cl, Br and I. Bromine and chlorine are preferred halo groups.

A sulfonic ester is a —OSO$_2$— group; and a sulfinic ester is an —SO—O— group.

A lower alkyl sulfonyl ester is a —OSO$_2$-lower alkyl and a lower alkyl sulfinyl ester is a —SO—O-lower alkyl, e.g., a mesylate.

A arylsulfonyl ester is a —OSO$_2$-aryl and an arylsulfinyl ester is a —SO—O-aryl wherein the aryl may be substituted with 1–3 lower alkyl groups, 1–2 halogens or 1–2 nitro groups, e.g., a tosylate or brosylate.

The substituents, if any, on R$^1$, R$^2$, R$^3$ and R$^4$ are preferably not α-substituents, and are preferably on the β-carbon atom, i.e., to yield β-chloroethyl or β-bromoethyl R$^1$, R$^2$, R$^3$ and/or R$^4$. Preferably, R$^1$ is the same as R$^2$ and R$^3$ is the same as R$^4$. In some preferred embodiments of the present compounds, R$^1$=R$^2$=R$^3$=R$^4$ and all four groups are β-chloroethyl or β-bromoethyl.

The compounds of the present invention can be prepared as shown in Scheme A, below.

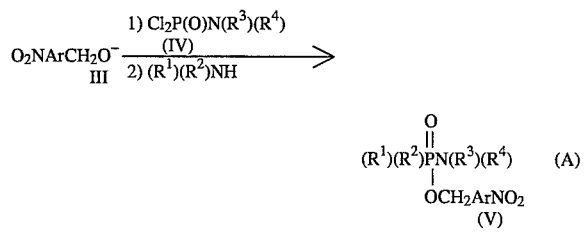

An alkoxide of Formula III is reacted with, for example, N,N-bis(2-haloethyl)phosphamidic dichloride (IV, R$^3$=R$^4$= 2-haloethyl), followed by the addition of ammonia or an amine (R$^1$)(R$^2$)NH, to form the compound of formula (V). For detailed procedures relating to these reactions, see Examples 1 and 2 of PCT application WO 89/11484. A wide variety of amines may be employed in Step 2, to yield the compounds of the present invention, many of which can be prepared from [bis(2-chloroethyl)]amine by methods known to the art. Compounds of Formula IV can be prepared by the reaction of bis(substituted amines) with $POCl_3$ in the presence of an organic base.

It is preferable that the reaction take place in an inert organic solvent such as methylene chloride, dioxane, tetrahydrofuran, hexane and the like. The reaction can take place at temperatures ranging from the melting point of the solvent to reflux temperatures, but it is preferred that the reaction take place from about −60° C. to room temperature.

The alkoxide of Formula III can be prepared by reacting the corresponding alcohol, $O_2N$—$ArCH_2OH$, with a strong base, such as alkali metal, an hydroxide or amide of an alkali metal, or a strong metal organic base, e.g., alkoxide, metal alkylamides, metal alkylsilylamides, e.g., lithium bis-trimethyl-silylamide and the like, or an organo-metallic compound, such as metallic alkyls, such as n-butyl lithium and the like, in accordance with procedures known to the art. The alcohol, $ArCH_2OH$, can be prepared by a variety of methods, e.g., reducing the corresponding aldehyde, e.g., with $NaBH_4$.

If $R^1$, $R^2$, $R^3$ and $R^4$ are 2-haloethyl, then phosphorus trichloride can be reacted with 2 equivalents of N,N-bis(2-haloethyl)amine hydrochloride in the presence of an alkylamine base. The alcohol produced from the above reaction can then be added followed by an oxidizing agent such as t-butyl hydroperoxide, ozone, or iodine to form one species of the final product, as shown in Scheme (B):

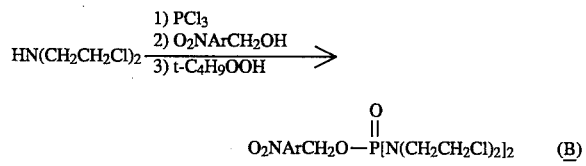

The compounds of the present invention can be formulated as pharmaceutical compositions and administered to a mammalian host, such as a human cancer patient, in a variety of forms adapted to the chosen route of administration, i.e., orally or parenterally, by intravenously, intramuscularly or subcutaneous routes.

Thus, the present phosphoramidate compounds may be orally administered, for example, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion use can include sterile aqueous solutions or dispersions or sterile powders comprising the active ingredient which are adapted for the extemporaneous preparation of sterile injectable or infusable solutions or dispersions. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersion or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful dosages of the compounds of I can be determined by comparing their in vitro activity, and in vivo activity in animal models, to that of an equivalent dosage of cyclophosphamide. For example, a compound of the present invention that is 10–20 times more potent than cyclophosphamide against a particular cancer may be administered intravenously in a dose of about 0.25–2.5 mg/kg/day for 2–5 days, a lower maintenance dosage is then continued, i.e., once or twice weekly, for As long as clinical improvement is evident. The dosage can be adjusted weekly according to the patient's tolerance.

The present analogs can be used to treat cancers known to be susceptible to cyclophosphamide, including, but not limited to, Burkitt's tumor, chronic lymphocytic leukemia, multiple myeloma, squamous cell and large cell anaplastic carcinomas, adenocarcinoma of the lung, Ewing's sarcoma, non-Hodgkins lymphoma, breast tumor, oat-cell bronchogenic carcinoma, squamous cell carcinoma of the cervix, ovarian tumors, bladder tumors, testicular tumors, endometrial tumors, malignant melanoma and acute lymphocytic leukemia, and prostatic carcinoma. The present compounds can be administered as single agents, or in combination with other antineoplastic drugs commonly employed with cyclophosphamide to treat these cancers. Pediatric dosage schedules may also be adapted from the regimens known to be effective in the case of cyclophosphamides.

The invention will be further described by reference to the following detailed examples.

EXAMPLE 1

Standard Procedure for the Preparation of Nitroarylmethyl N,N,N',N'-tetrakis(2-chloroethyl)phosphoramidates Phosphorus trichloride (5.0 mL, 2.0M in dichloromethane, 10 mmol) is added to dichloromethane (100 mL) and cooled to 0° C. Bis-(2-chloroethyl)-amine hydrochloride (3.8 g, 21 mmol) is added with stirring. Triethylamine (8.5 mL, 61 mmol) is added dropwise via syringe over 5 minutes and the resulting mixture stirred 10 minutes. The nitroarylmethyl alcohol is dissolved in 20 mL of dichloromethane and added all at once to the reaction mixture. The mixture is stirred for 10 minutes and cooled to −20° C. t-Butyl hydroperoxide solution (3.5 mL, 11 mmol) is added and the bath allowed to warm to room temperature. Ethyl acetate (100 mL) is added and the mixture filtered. The filtrate is washed with 5% citric acid (250 mL), and finally with water (250 mL), followed by drying (MgSO$_4$) and concentration. The residue is purified by flash chromatography on silica gel.

A. (5-Nitro-2-thiophenyl)methyl-N,N,N',N'-tetrakis(2-chloroethyl)phosphoramidate (1).

The residue was chromatographed (1:19 acetone:dichloromethane) to give 1 (52%) as a brown solid. m.p. 44° C.; R$_f$=0.60.

$^1$H NMR (CDCL$_3$ δ 7.82 (1H, d, J=3.9), 7.05 (1H, d, J=3.9), 5.23 (2H, d, J=7.8), 3.68 (8H, m), 3.41 (8H, m).

$^{31}$P NMR (CDCl$_3$) δ −8.08 (s).

IR (KBr) 3105, 2963, 2879, 1541, 1504, 1446, 1341, 1220, 1149, 1129, 1020, 982, 920, 890, 817, 762, 736, 659 cm$^{-1}$.

B. (5-Nitro-2-furanyl)methyl-N,N,N',N'-tetrakis(2-chloroethyl)phosphoramidate (2).

The residue was chromatographed (1:19 acetone:dichloromethane) to give 2 (49%) as a brown oil.

R$_f$=0.55

$^1$H NMR (CDCL$_3$) δ 7.29 (1H, d, J=3.7), 6.68 (1H, d, J=3.7), 5.10 (2H, d, J=9.0), 6.50 (8H, m), 3.45 (8H, m).

$^{31}$P NMR (CDCL$_3$) δ −7.57 (s).

IR (neat) 3139, 2968, 2882, 1774, 1728, 1599, 1537, 1505, 1456, 1400, 1354, 1245, 1230, 1150, 1132, 1090, 1020, 972, 924, 895, 815, 760, 660 cm$^{-1}$.

C. (1-Methyl-5-nitro-2-imidazolyl)methyl-N,N,N',N'-tetrakis-( 2-chloroethyl)phosphoramidate (3).

The residue was chromatographed (1:19 acetone:dichloromethane) to give 3 (73%) as a brown oil. R$_f$= 0.38.

$^1$H NMR (CDCL$_3$) δ 7.99 (1H, s), 5.18 (2H, d, J=8.2), 4.07 (3H, s), 3.66 (8H, m), 3.44 (8H, m).

$^{31}$P NMR (CDCl$_3$) δ −7.69 (s).

IR (KBr) 2970, 1536, 1477, 1383, 1361, 1350, 1272, 1245, 1226, 1196, 1250, 1198, 1152, 1134, 1090, 1028, 984, 926, 894, 865, 832, 750 cm$^{-1}$.

D. (N-Methyl-4-nitro-2-pyrrolo)methyl-N,N,N',N'-tetrakis-( 2-chloroethyl)phosphoramidate (4).

The residue was chromatographed (1:19 acetone:dichloromethane) and rechromatographed (1:3 ethyl acetate:hexanes) to give 4 (55%) as a brown oil. R$_f$=0.50.

$^1$H NMR (CDCL$_3$) δ 7.55 (1H, d, J=1.8), 6.82 (1H, d, J=1.8) 5.02 (2H, d, J=7.7), 3.76 (3H, s), 3.62 (8H, m), 3.40 (8H, m).

$^{31}$P NMR (CDCl$_3$) δ −8.28.

IR (neat) 3110, 2960, 2860, 1718, 1607, 1528, 1490, 1435, 1410, 1341, 1302, 1272, 1232, 1211, 1145, 1122, 1096, 1083, 998, 971, 945, 915, 887, 842, 820, 790, 768, 752, 718, 653 cm$^{-1}$.

EXAMPLE 2

(5-Nitro-2-thiophenyl)methyl-N,N-bis(bromoethyl)-phosphoramidate (6)

A solution of 5-nitro-2-hydroxymethylthiophene (10 mmol) in dry THF (20 mL) was added to a solution of lithium bis(trimethylsilyl)amide (11 mL of 1M in THF, 11 mmol) at −78° C. The solution was stirred for 5 min, and a solution of bis(2-bromoethyl)phosphoramidic dichloride (12 mmol) in dry THF (24 mL) was added slowly. The mixture was stirred for 2 hr at −78° C. and then warmed to −20° C. Anhydrous ammonia gas was passed through the reaction mixture for 10 min, the mixture was warmed to room temperature, and the excess ammonia was neutralized with 1N HCl. The resulting mixture was extracted with ethyl acetate (3×40 mL), and the combined extracts were dried (MgSO$_4$), filtered and evaporated in vacuo. The residue was subjected to flash chromatography on silica gel, using 1:20 methanol:ethyl acetate as eluent to yield 6.4 mmol of 6 (64%); $^1$H NMR (CDCl$_3$) δ 7.83 (1H, d), 7.03 (1H, d), 5.20 (2H, m), 3.51 (8H, m), 2.89 (2H, bs); $^{31}$P NMR (CDCl$_3$) δ −9.06 (s).

EXAMPLE 3

(5-Nitro-2-thiophenyl)methyl-N,N-bis(chloroethyl)phosphoramidate (7) was prepared as described for 6 above, except that bis(2-chloroethyl)phosphoramidic dichloride was used in place of bis(2-bromoethyl)phosphoramidic dichloride to yield 7 in 46% yield: $^1$H NMR (CDCl$_3$) δ 7.91 (1H, d), 7.03 (1H, d), 5.18 (2H, t), 3.70 (4H, m), 3.44 (4H, m), 2.91 (2H, bs); $^{31}$P NMR (CDCl$_3$) δ 8.52 (s).

EXAMPLE 4

(5-Nitro-2-furyl)methyl-N,N-bis(chloroethyl)phosphoramidate (8) is prepared as described for 6 above, except that 5-nitro-2-hydroxymethylfuran is used in place of 5-nitro-2-hydroxymethylthiophene, and bis(2-chloroethyl)phosphoramidic dichloride is used in place of bis(2-bromoethyl)phosphoramidic dichloride: $^1$H-NMR(CDCl$_3$):δ7.26 (1H, d), 6.64 (1H, d), 5.07 (1H, s), 5.04 (1H, s), 3.67 (4H, m), 3.5 (4H, m), 3.03 (2H, bs); $^{31}$P-NMR (CDCl$_3$): δ −2.17 (s).

EXAMPLE 5

(5-Nitro-2-furyl)methyl N,N-bis(bromoethyl)phosphoramidate (9) was prepared as described above, except that 5-nitro-2-hydroxymethylfuran was used in place of 5-nitro-2-hydroxymethylthiophene to yield 5.6 mmol of 9 (56%); $^1$H NMR (CDCl$_3$) δ 7.29 (1H, d), 6.66 (1H, d), 5.06 (2H, d), 3.51 (8H, m), 2.83 (2H, bs); $^{31}$P NMR (CDCl$_3$) δ −8.63 (s).

EXAMPLE 6

Cytotoxicity of Phosphoramidates

A. Protocol for Evaluation of Cytotoxicity against B16 Melanoma Cells

B16 melanoma cells in exponential growth (2–3×10$^6$ cells in 10 ml of serum-free MEM medium) were treated with drug for 2 hr. The cells were separated, washed, and resuspended in MEM medium supplemented with 10% fetal bovine serum. The cells were plated in 60-mm culture dishes at a density of 50–50,000 cells/plate (depending upon the drug concentration used) and then incubated for 8 days in a CO$_2$ incubator at 37° C. The colonies were fixed and stained with 0.5% crystal violet in ethanol and counted. The log of the surviving fraction was plotted against drug concentration, and from this plot, the concentration required to reduce the colony number to 1% of control (LC$_{99}$) was determined.

The results of this test on representative compounds of the present invention was tabulated in Table 2.

B. Protocol for Evaluation of Aerobic and Hypoxic Selectivity Against Human Colon Cancer HT29 Cells HT29 human colon cancer cells were maintained in exponential growth in α-MEM medium supplemented with 10% fetal bovine serum and 25 mM HEPES buffer, and cultured at 37° C. and 3% CO$_2$. For drug treatments, 1–2×10$^6$ cells in 10 ml of medium were transferred to glass reaction vials. For the hypoxic experiments, the medium was first gassed for 3 hr with 95% nitrogen/5% CO$_2$ to achieve a partial pressure of oxygen less than 100 ppm. These cell suspensions were then treated with drug at different concentrations under either aerobic or hypoxic conditions for 4 hr in the reaction vials. The medium was removed, the cells were washed, and a colony-formation assay was carried out using the soft agar colony-forming assay of Chu and Fischer, *Biochem. Pharmacol.*, 17, 753–767 (1968). Typically, HT29 cells (2–3×10$^6$ cells/ml) in exponential growth and suspended in 6.5 ml of Fischer's medium (Gibco Lab., Grand Island, N.Y.) were divided into six groups (1 control and 5 treated groups) containing an equal number of cells in 1 ml. These cells were then treated with varying doses of drug diluted with media to give a total volume of 10 ml, and incubated for four hours at 37° C. The cells were washed three times with 3 ml of supplemented Fischer's medium (containing 10% horse serum) by centrifugation (800×g), removal of media by suction, and resuspension of the pellet in media (5 ml). A 1 ml portion was used to determine the cell count with a Coulter counter. From the remainder, a 5-ml suspension of cells was prepared at a density of 10$^5$ cells/ml, and between 10$^2$ and 10$^5$ cells were placed on soft agar and incubated at 37° C.

C. Protocol for Evaluation of Cytotoxicity Against Parental (/O) and Cyclophosphamide-resistant (/CP) MCF-7 Human Breast Cancer Cells.

MCF-7 human breast carcinoma cells are grown as monolayers in Dulbecco's MEM medium supplemented with 10% fetal bovine serum, L-glutamine, and pen/strep antibiotics at 37° C. and in the presence of 5% CO$_2$. Parental MCF-7 cells or a cloned cyclophosphamide-resistant subline in exponential growth were treated with various concentrations of the drugs. After exposure to the drug or vehicle for 2 hr in serum-free media, the cells were washed 3 times with serum-free media and plated in quintuplicate at 3 dilutions for colony formation. After 13 days, the colonies were visualized by staining with crystal violet, and colonies of at least 50 cells were counted. The log of the surviving fraction was plotted against drug concentration, and from this plot, the concentration required to reduce the colony number to 1% of control (LC$_{99}$) was determined. The results of this test on representative compounds of the present invention are tabulated in the Table 2.

D. Results

TABLE 2

Compound Concentration (μM) Required to Kill 99% of Clonogenic Tumor Cells In Vitro

| Compound | B16 (LC$_{99}$) | HT29 (LC$_{99}$) | | MCF-7 (LC$_{99}$) | |
|---|---|---|---|---|---|
| | | Aerobic | Hypoxic | /O[1] | /cp[2] |
| HPCP[3] | 12.0 | nd[a] | nd | 14.0 | 145.0 |
| <u>1</u> | 5.8 | 11 | 7 | 7.0 | 9.2 |
| <u>2</u> | 9.2 | 13 | 4 | 20 | 22 |
| <u>3</u> | 144 | >300 | 25 | nd | nd |
| <u>4</u> | 37 | 144 | 65 | >300 | >300 |
| <u>6</u> | 1.9 | nd | nd | 6.1 | 4.1 |
| <u>7</u> | 5.1 | nd | nd | 9.8 | 8.2 |
| <u>8</u> | 9.7 | nd | nd | nd | nd |
| <u>9</u> | 1.8 | nd | nd | 5.4 | 3.0 |

[a]Not tested.
[1]Cyclophosphamide-sensitive parental cells.
[2]Cyclophosphamide-resistant cells.
[3]Hydroperoxycyclophosphamide.

All publications, patents and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A method of treating a solid tumor in a mammalian host comprising administering to said host a pharmaceutical unit dosage form comprising an amount of a compound of the formula:

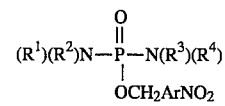

wherein R$^1$ and R$^2$ are individually (C$_2$–C$_6$)alkyl, optionally substituted with halogen, (C$_1$–C$_4$)alkoxy, (C$_6$–C$_{12}$)aryloxy, cyano, (C$_1$–C$_4$)alkoxycarbonyl, (C$_1$–C$_4$)alkylsulfonyl, (C$_6$–C$_{12}$)arylsulfonyl, (C$_1$–C$_4$)perfluoroalkylsulfonyl, (C$_1$–C$_{c4}$)alkylsulfinyl, (C$_6$–C$_{12}$)arylsulfinyl, or R$^1$ and R$^2$ taken together with N are a morpholino ring; R$^3$ and R$^4$ are the same as R$^1$ and R$^2$ or are individually H; and Ar is a sulfur- or oxygen-containing heteroaromatic ring; in combination with a pharmaceutically acceptable vehicle, which amount is effective to inhibit the growth of said solid tumor, wherein said tumor is a lung adenocarcinoma, a breast tumor, an ovarian tumor, a malignant melanoma or a colon tumor.

2. The method of claim 1 wherein the dosage form is administered parenterally.

3. The method of claim 1 wherein the dosage form is administered orally.

4. The method of claim 1 wherein $R^1$ and $R^2$ are $(C_2-C_4)$alkyl substituted with halogen.

5. The method of claims 1 wherein $R^3$ and $R^4$ are $(C_2-C_4)$alkyl substituted with halogen, or are H.

6. The method of claim 1 wherein Ar is a 5- or 6-membered heteroaromatic ring comprising 1–3, S or non-peroxide O atoms in the ring.

7. The method of claim 6 wherein $ArNO_2$ is a 5-nitro-2-thiophenyl, or 5-nitro-2-furanyl.

8. The method of claim 7 wherein $R^1$, $R^2$, $R^3$ and $R^4$ are the same.

9. The method of claim 8 wherein $R^1$, $R^2$, $R^3$ and $R^4$ are 2-haloethyl.

10. The method of claim 7 wherein $R^1$ and $R^2$ are 2-haloethyl and $R^3$ and $R^4$ are H.

11. The method of claim 1 wherein the compound is (5-nitro-2-thiophenyl)methyl-N,N,N' ,N'-tetrakis(2-chloroethyl)phosphoramidate.

12. The method of claim 1 wherein the compound is (5-nitro-2-furanyl)methyl-N,N,N' ,N'-tetrakis(2-chloroethyl)phosphoramidate.

* * * * *

UNITED STATES PATENT AND TRADEMARK OFFICE
CERTIFICATE OF CORRECTION

PATENT NO. : 5,472,956

DATED : December 5, 1995

INVENTOR(S) : Borch et al.

It is certified that error appears in the above-identified patent and that said Letters Patent is hereby corrected as shown below:

In Column 8, line 56, please delete --δ 8.52-- and insert "δ -8.52"

In Column 10, line 34, please delete --Hydroperoxycyclophosphamide-- and insert "4 Hydroperoxycyclophosphamide"

In Column 10, line 61, please delete --$C_{c4}$-- and insert "$C_4$"

Signed and Sealed this

Seventeenth Day of June, 1997

*Attest:*

BRUCE LEHMAN

*Attesting Officer*  Commissioner of Patents and Trademarks